US012626614B2

(12) United States Patent
Mahn et al.

(10) Patent No.: US 12,626,614 B2
(45) Date of Patent: May 12, 2026

(54) SOFT TISSUE SURGICAL TASK TRAINER

(71) Applicant: University of Florida Research Foundation, Inc., Gainesville, FL (US)

(72) Inventors: Savanna Mahn, Gainesville, FL (US); Ceri Borde, Gainesville, FL (US); Brian B. Hughley, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 726 days.

(21) Appl. No.: 17/919,139

(22) PCT Filed: May 5, 2021

(86) PCT No.: PCT/US2021/030774
§ 371 (c)(1),
(2) Date: Oct. 14, 2022

(87) PCT Pub. No.: WO2021/226164
PCT Pub. Date: Nov. 11, 2021

(65) Prior Publication Data
US 2023/0169889 A1 Jun. 1, 2023

Related U.S. Application Data

(60) Provisional application No. 63/020,588, filed on May 6, 2020.

(51) Int. Cl.
*G09B 23/30* (2006.01)
*A61L 31/12* (2006.01)

(52) U.S. Cl.
CPC .............. *G09B 23/30* (2013.01); *A61L 31/12* (2013.01)

(58) Field of Classification Search
CPC ...................................................... G09B 23/30
See application file for complete search history.

(56) References Cited

U.S. PATENT DOCUMENTS

| | | | |
|---|---|---|---|
| 6,780,016 | B1 | 8/2004 | Toly |
| 2014/0045161 | A1 | 2/2014 | Nguyen |
| 2021/0049932 | A1 | 2/2021 | Powdrill et al. |

OTHER PUBLICATIONS

ISR Mailed Aug. 6, 2021, Application No. PCT/US2021/030774 filed May 5, 2022, (pp. 1-11).

*Primary Examiner* — Jerry-Daryl Fletcher
(74) *Attorney, Agent, or Firm* — Thomas | Horstemeyer, LLP

(57) ABSTRACT

The disclosure relates to a simulated tissue useful as a surgical training aid, the simulated tissue including at least the following: (a) a skin layer, (b) a fat layer, (c) a muscle layer, (d) a first mesh, (e) an interstitial layer, (f) a second mesh, (g) a structural layer incorporating one or more anatomical components, and (h) a base layer. Methods for constructing the simulated tissue are also disclosed. The simulated tissues described herein can be used as a soft tissue surgical task trainer for numerous surgical procedures.

18 Claims, 1 Drawing Sheet

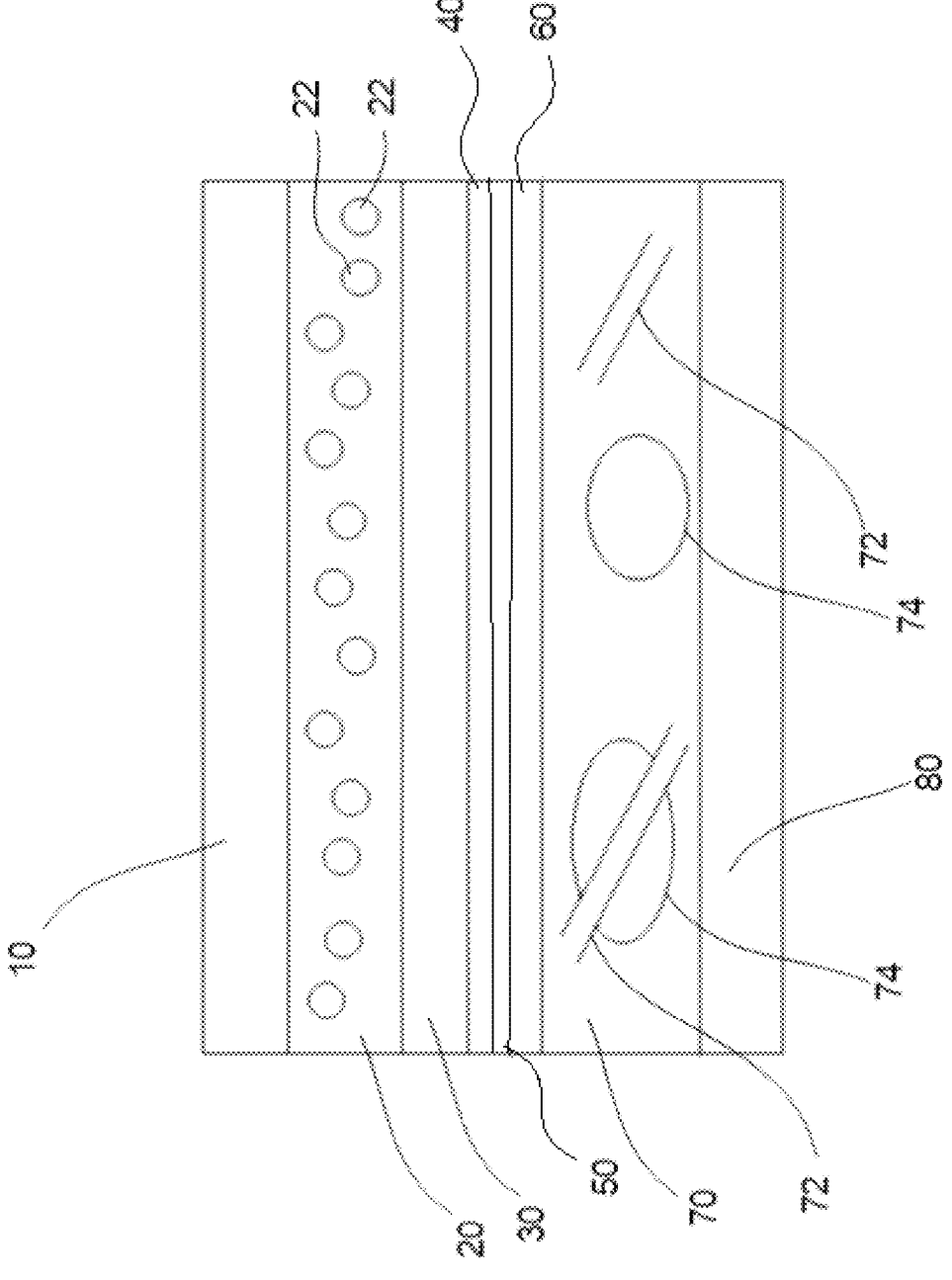

SOFT TISSUE SURGICAL TASK TRAINER

CROSS-REFERENCE TO RELATED APPLICATIONS

This application is the 35 U.S.C. § 371 national stage of PCT application having serial number PCT/US2021/030774, filed on May 5, 2021, which claims priority to U.S. provisional application entitled "SOFT TISSUE SURGICAL TASK TRAINER," having Ser. No. 63/020,588 filed on May 6, 2020, which are entirely incorporated herein by reference.

BACKGROUND

Doctors and medical students are subjected to extensive training in any new surgical technique before practicing the same on human patients. Any such training method should involve the use of the same tools that would be employed during an actual surgery on a patient including, but not limited to, scalpels, scissors, forceps, clamps, needles and suture, retractors, suction instruments, staplers and clips, and other instruments. Furthermore, any such training method must account for differences in human anatomy. For example, tumors can have different sizes, locations, and levels of vascularization; patients can have different body weights as well as different thicknesses of subcutaneous muscle and fat; and so forth. Thus, an ideal surgical training aid should be customizable to mimic different patient body types and different tumor sizes, among other parameters.

Surgeries for the neck area can be particularly important to practice due to the close proximity of several major arteries and veins, nerves, the trachea, the esophagus, the larynx, the thyroid and parathyroid glands, and other structures. Other soft tissues including the male urogenital tract, the gastrointestinal tract, and the like, present similar challenges. A method for constructing a surgical training aid would ideally be adaptable to different thicknesses and shapes of tissue in order to enable practice for surgeons and students on different areas of the body.

It would be desirable if the surgical training aid was made from inexpensive and readily-available materials. It would further be desirable if the surgical training aid simulated the feel and responsiveness of human tissue, including different densities and levels of resistance to cutting in layers of the training aid meant to represent different layers of human tissue (e.g., muscle, skin, fat, and the like). The present disclosure addresses these needs.

SUMMARY

In accordance with the purpose(s) of the present disclosure, as embodied and broadly described herein, the disclosure, in one aspect, relates to a simulated tissue useful as a surgical training aid, the simulated tissue including: (a) a skin layer having a first surface and second surface; (b) a fat layer having a first surface and second surface, wherein the first surface of the fat layer is adjacent to the second surface of the skin layer; (c) a muscle layer having a first surface and second surface, wherein the first surface of the muscle layer is adjacent to the second surface of the fat layer; (d) a first mesh having a first surface and second surface, wherein the first surface of the first mesh is adjacent to the second surface of the muscle layer; (e) an interstitial layer having a first surface and second surface, wherein the first surface of the interstitial layer is adjacent to the second surface of the first mesh; (f) a second mesh having a first surface and second surface, wherein the first surface of the second mesh is adjacent to the second surface of the interstitial layer; (g) a structural layer incorporating one or more anatomical components adjacent to the second surface of the second mesh; and (h) a base layer having a first surface and second surface, wherein the first surface of the base layer is adjacent to the structural layer. Methods for constructing the simulated tissue are also disclosed.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 shows a schematic of the cross-sectional view of a simulated tissue disclosed herein.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a pigment," "a silicone," or "a tactile modifier," includes, but is not limited to, mixtures of two or more such pigments, silicones, or tactile modifiers, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a tactile modifier refers to an amount that is sufficient to achieve the desired improvement in the property modulated by the formulation component, e.g. achieving the desired color. The specific level in terms of wt % in a composition required as an effective amount will depend upon a variety of factors including the amount and type of silicone, amount and type of pigment, if any, contact with any other layers including mesh, simulated tumors, simulated vessels, or the like, and desired texture of the simulated tissue in which the tactile modifier is included.

As used herein, the terms "optional" or "optionally" means that the subsequently described event or circumstance can or cannot occur, and that the description includes instances where said event or circumstance occurs and instances where it does not.

"Shore hardness" as used herein is a measure of the resistance of a material to indentation. Different scales exist for measuring the hardness of different materials and are typically separated based on durometer type (e.g., for the A scale, the durometer is a 35° truncated cone with a 1.40 mm diameter, a 2.54 mm extension, and an 8.05 N spring force). The final value of Shore hardness is the depth of the indenter after it is applied to the material for 15 seconds.

"Platinum cure silicone" or "addition cure silicone" is a two component, flexible molding or casting compound. Platinum cure silicones typically have high tensile strengths and high tear strengths and generate no peroxide residues. In one aspect, latex, sulfur, tin-cure silicone, and other products may inhibit curing of platinum cure silicone and thus the work area should be free of these compounds when pouring the silicone layers disclosed herein. Platinum cure silicone is able to withstand extreme conditions (moisture, radiation, high temperature) and exhibits low shrinkage and a wide range of hardnesses. In one aspect, platinum cure silicone is thus named because a platinum complex catalyst is required for curing.

As used herein, "pot life" refers to the amount of time it takes for an initial mixed viscosity to double (e.g., in a two-part platinum cure silicone). Pot life is typically measured at room temperature.

As used herein, "cure time" refers to the amount of time required for a system to fully cure. In one aspect, the silicones useful herein exhibit a wide variety of cure times. In some aspects, the silicones used in different layers of the simulated tissue disclosed herein have different cure times.

As used herein, "specific gravity" is also sometimes referred to as "relative density" and is the ratio of the density of a substance to the density of a standard, which is typically water. In one aspect, the silicones useful herein have specific gravities of around 1, meaning they are approximately as dense as water, though individual values for polymer systems may be a little above or a little below 1.

"Viscosity" as used herein is a measure of the resistance to a fluid to deformation at a given rate. Liquids that appear thicker typically have higher viscosities than liquids that appear thinner. Silicones with a variety of uncured/liquid viscosities are useful in the applications disclosed herein.

"Tensile strength" as used herein is the maximum stress a material, such as a cured silicone, can withstand while being stretched or pulled. If the tensile strength of the material is exceeded, the material will break or tear.

Unless otherwise specified, temperatures referred to herein are based on atmospheric pressure (i.e. one atmosphere).

In one aspect, disclosed herein is a simulated tissue. In a further aspect, the simulated tissue can be used as a soft tissue surgical task trainer for ear, nose, and throat (ENT) surgeons to practice techniques using specific surgical tools. In a further aspect, techniques that can be practiced on the soft tissue surgical task trainer disclosed herein include, but are not limited to, removal of fascia, tumor removal, suturing, incisions, and the like. In one aspect, internal jugular central venous catheter placement can be practiced on the soft tissue surgical task trainer disclosed herein. In still another aspect, the soft tissue surgical task trainer can be constructed to simulate components of the gastrointestinal tract and/or any other system or organ that includes soft tissues. Also disclosed herein are methods for constructing the simulated tissue.

Individual components and layers of the simulated tissue are discussed in detail below.

Silicone Rubber

In one aspect, a silicone compounds such as, for example, a silicone rubber can be used to construct the simulated tissue. In one aspect, the silicone rubber can be an ECO-FLEX™ silicone or a DRAGONSKIN™ silicone (Smooth-On, Macungie, PA). In a further aspect, the silicone can have a Shore hardness of 2A, 5A, 10A, 20A, 30A, OO-10, OO-20, OO-30, OO-33, OO-35, OO-50, or OOO-35. Other Shore hardness values are also contemplated and should be considered disclosed.

In some aspects, the silicones are platinum cured silicones and are provided in two parts that are mixed in equal volumes. In a further aspect, these parts are mixed thoroughly and degassed in a vacuum for best results.

In a further aspect, following mixing, the silicone can have a pot life of from about 1 minute to about 45 minutes, or of about 1, 2, 2.5, 3, 4, 5, 8, 12, 15, 18, 20, 25, 30, 35, or about 40 minutes, or a combination of any of the foregoing values, or a range encompassing any of the foregoing values.

In another aspect, the silicone can have a cure time of from about 5 min to about 16 h, or of about 5, 10, 15, 20, 25, 30, 35, 40, 45, 50, 55, 60, 65, 70, or 75 min, or of about 2, 3, 4, 5, 6, 7, 8, 9, 10, 11, 12, 13, 14, 15, or about 16 h, or a combination of any of the foregoing values, or a range encompassing any of the foregoing values.

In another aspect, the silicone should be stored and can be cured at room temperature and has a useful range of from about −65° F. to about 450° F. In some aspects, following curing, the silicones can be exposed to higher temperatures according to the following scheme: (i) 176 ° F. for 2 h, and (ii) 212° F. for 1 h. Further in these aspects, such heat treatment can aid in quickly attaining maximum physical performance properties for the silicones.

In one aspect, the mixed silicones prior to curing have a specific gravity of from about 0.95 to about 1.1 g/cc, or of about 0.95, 1, 1.05, or about 1.1 g/cc, or a combination of any of the foregoing values, or a range encompassing any of the foregoing values. In one aspect, the specific gravity is about 0.98, 1.04, 1.062, 1.07, or about 1.08 g/cc.

In another aspect, the mixed silicones prior to curing have a viscosity of from about 3000 to about 23,000 cps, or of about 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, or about 23,000 cps, or a combination of any of the foregoing values, or a range encompassing any of the foregoing values.

In still another aspect, the mixed silicones once cured have a tensile strength of from about 100 to about 600 psi, or of about 100, 150, 200, 250, 300, 350, 400, 450, 500, 550, or about 600 psi, or a combination of any of the foregoing values, or a range encompassing any of the foregoing values. In one aspect, the tensile strength is about 120, 160, 200, 288, 315, 350, 400, 475, 500, or about 550 psi.

Tactile Modifier

In one aspect, the silicones useful herein can be modified with one or more tactile modifiers. In a further aspect, the tactile modifier can increase or decrease the viscosity of the mixed silicone and/or impart a different texture, elasticity, or resilience to the cured silicone, such as, for example, by altering the rebound properties of the silicone to make it feel more like human tissue. In one aspect, SLACKER TAC-TILE MUTATOR® (Reynolds Advanced Materials, Macungie, PA) is useful as a tactile modifier in the formulations disclosed herein. In a further aspect, the tactile modifier can be added to the silicones in any desired ratio such as, for example, 5:1 to 1:5 silicone: tactile modifier, or about 5:1, 5:1, 3:1, 2:1, 1:1, 1:2, 1:3, 1:4, or about 1:5, or a combination of any of the foregoing values, or a range encompassing any of the foregoing values.

In another aspect, when a pigment and a tactile modifier are both used, the pigment is added to the silicone prior to the addition of the tactile modifier. In some aspects, the tactile modifier prior to mixing with the silicone can have a viscosity of about 10,000 cps.

Mesh

In some aspects, the simulated tissues disclosed herein incorporate at least one mesh. In a further aspect, the mesh can be woven from monofilament synthetic fibers. In some aspects, the mesh can be an industrial textile with narrow pore distribution. In one aspect, the mesh has a hole size as low as 50 µm, although other mesh dimensions are possible. In a still further aspect, the mesh can have a plain weave, a twill weave, a satin weave, or can be a hex mesh.

In one aspect, the mesh can be woven from a nylon, polyester, polypropylene, polyvinylidene fluoride, polyurethane, polyethylene, a vinyl coated polyester, a thermoplastic elastomer, another monofilament, or a combination thereof.

Pigment

In some aspects, the silicones and other materials disclosed herein are translucent, off-white translucent, water white translucent, or a combination thereof. In one aspect, the silicones are used as-is without any pigment. In an alternative aspect, pigments can be added to the silicones to impart colors to the various layers of the simulated tissue (i.e., skin in a flesh-toned pigment, fat with a yellow-toned pigment, muscle with a red-toned pigment, etc.). In one aspect, the pigments can be SILC PIG™ pigments (Smooth-On, Macungie, PA). In a further aspect, the SILC PIG™ pigments are present in an amount of from about 0.001% to about 3% of total silicone weight, or at about 0.001, 0.005, 0.01, 0.05, 0.1, 0.5, 1, 2, or about 3% of total silicone weight, or a combination of any of the foregoing values, or a range encompassing any of the foregoing values. In some aspects, increasing pigment level above about 3% of total silicone weight may inhibit the curing of the silicone. In a further aspect, the pigment can be a viscous liquid or paste in a non-aqueous carrier that is mixed by hand or by machine into the silicone in question.

Layers of Simulated Tissue

In one aspect, disclosed herein is a simulated tissue including at least the following components: (a) a skin layer with a first surface and second surface, wherein the skin layer comprises a silicone rubber and a tactile modifier; (b) a fat layer with a first surface and second surface, wherein the first surface of the fat layer is adjacent to the second surface of the skin layer, and wherein the fat layer includes a silicone rubber and a tactile modifier; (c) a muscle layer having a first surface and second surface, wherein the first surface of the muscle layer is adjacent to the second surface of the fat layer, and wherein the muscle layer includes a silicone rubber; (d) a first mesh having a first surface and second surface, wherein the first surface of the first mesh is adjacent to the second surface of the muscle layer; (e) an interstitial layer having a first surface and second surface, wherein the first surface of the interstitial layer is adjacent to the second surface of the first mesh, and wherein the interstitial layer includes a silicone rubber and a tactile modifier; (f) a second mesh with a first surface and second surface, wherein the first surface of the second mesh is adjacent to the second surface of the interstitial layer; (g) a structural layer that includes one or more anatomical components adjacent to the second surface of the second mesh; and (h) a base layer with a first surface and second surface, wherein the first surface of the base layer is adjacent to the structural layer, and wherein the base layer includes a silicone rubber.

A schematic drawing according to one aspect of the disclosed simulated tissue is shown in FIG. 1. Skin layer 10 directly contacts (i.e., adjacent to) fat layer 20. Fat layer 20 may be constructed with a plurality of lumps 22 to more closely approximate the structure of human fat. In one aspect, the lumps may not have discrete, regular shapes. Beneath fat layer 20 is muscle layer 30, which is in contact with the first mesh 40. Interstitial layer 50 may exist between first mesh 40 and second mesh 60. Beneath second mesh 60 is structural layer 70, which may contain one or more vessels 72. In some aspects, the vessels 72 are associated with anatomical components 74 (such as, for example, organs or tumors, although other components are also envisioned, as disclosed herein) and in other aspects the vessels 72 are meant to be traversing the tissue to supply blood to the tissue and/or to adjacent organs. Beneath and in contact with structural layer 70 is base layer 80.

Skin Layer

In one aspect, in the simulated tissue disclosed herein, the skin layer has a thickness of from about 0.1 cm to about 1 cm, or of about 0.1, 0.2, 0.3, 0.4, 0.5, 0.6, 0.7, 0.8, 0.9, or about 1 cm, or a combination of any of the foregoing values, or a range encompassing any of the foregoing values.

In a further aspect, the skin layer includes a mixture of silicone rubber and tactile modifier in a ratio of from about 1:1 to about 4:1 by volume, or of about 1:1, 2:1, 3:1, or about 4:1 by volume, or a combination of any of the foregoing values, or a range encompassing any of the foregoing values. In one aspect, the ratio is about 2:1.

In some aspects, the skin layer also includes a flesh-toned pigment. In other aspects, the skin layer can include other combinations of pigments to represent different colors of flesh (e.g., brown, yellow undertones, green undertones, red undertones) to simulate different races.

Fat Layer

In one aspect, in the simulated tissue disclosed herein, the fat layer has a thickness of from about 0.25 cm to about 2 cm, or of about 0.25, 0.5, 0.75, 1, 1.25, 1.5, 1.75, or about 2 cm, or a combination of any of the foregoing values, or a range encompassing any of the foregoing values.

In another aspect, the fat layer includes a mixture of silicone rubber and tactile modifier in a ratio of from about 2:1 to about 1:2 by volume, or of about 2:1, 1.5:1, 1:1, 1:1.5, or about 1:2, or a combination of any of the foregoing values, or a range encompassing any of the foregoing values. In one aspect, the ratio is about 1:1.5.

In some aspects, the fat layer also includes a pigment. In one aspect, the pigment is yellow-toned to resemble the color of fat.

Muscle Layer

In one aspect, in the simulated tissue disclosed herein, the muscle layer has a thickness of from about 0.1 to about 1.5 cm, or of about 0.1, 0.2, 0.3, 0.4, 0.5, 0.6, 0.7, 0.8, 0.9, 1, 1.1, 1.2, 1.3, 1.4, or about 1.5 cm, or a combination of any of the foregoing values, or a range encompassing any of the foregoing values.

In some aspects, the muscle layer further includes a red-toned, a blood red pigment, or a combination thereof.

First Mesh

In one aspect, in the simulated tissue disclosed herein, the first mesh can be made from any fibrous material as disclosed herein. In one aspect, the first mesh can be woven from nylon, polyester, polypropylene, polyvinylidene fluoride, polyurethane, polyethylene, a vinyl coated polyester, a thermoplastic elastomer, another monofilament, or a combination thereof. In one aspect, the first mesh can be cut from a consumer product such as, for example, nylon pantyhose.

Interstitial Layer

In another aspect, in the simulated tissue disclosed herein, the interstitial layer has a thickness of from about 0.2 cm to about 1 cm, or of about 0.2, 0.3, 0.4, 0.5, 0.6, 0.7, 0.8, 0.9, or about 1 cm, or a combination of any of the foregoing values, or a range encompassing any of the foregoing values.

In a further aspect, the interstitial layer includes a mixture of silicone rubber and tactile modifier in a ratio of from about 2:1 to about 1:2 by volume, or of about 2:1, 1.5:1, 1:1, 1:1.5, or about 1:2 by volume, or a combination of any of the foregoing values, or a range encompassing any of the foregoing values. In one aspect, the ratio is about 1:1.

Second Mesh

In one aspect, in the simulated tissue disclosed herein, the second mesh can be made from any fibrous material as disclosed herein. In one aspect, the second mesh can be woven from nylon, polyester, polypropylene, polyvinylidene fluoride, polyurethane, polyethylene, a vinyl coated polyester, a thermoplastic elastomer, another monofilament, or a combination thereof. In one aspect, the second mesh can be cut from a consumer product such as, for example, nylon pantyhose.

Anatomical Components and Structural Layer

In a further aspect, the anatomical components disclosed herein are adhered to the second surface of the second mesh with a mixture that includes a silicone rubber and a tactile modifier. In one aspect, the silicone rubber and tactile modifier are present in a ratio of from about 2:1 to about 1:2 by volume, or of about 2:1, 1.5:1, 1:1, 1:1.5, 1:2, or a combination of any of the foregoing values, or a range encompassing any of the foregoing values. In one aspect, the ratio is about 1:1.

In some aspects, the mixture adhering the second surface of the second mesh to the anatomical components disclosed herein includes a white-toned pigment.

In another aspect, the anatomical component can be a simulated or artificial vein, organ, tumor, bone, duct, or any combination thereof. In some aspects, in the simulated tissue disclosed herein, the anatomical components are consistent with the structure of the neck and/or the jugular vein. In other aspects, the simulated tissue can be certain areas or regions of the body such as, for example, pelvic, femoral, popliteal regions.

In an alternative aspect, the anatomical component can be a component of the male urogenital system including, but not limited to, the vas deferens, urethra, or the like.

In one aspect, in the simulated tissue disclosed herein, the structural layer has a thickness of from about 0.5 cm to about 5 cm, or of about 0.5, 1, 1.5, 2, 2.5, 3, 3.5, 4, 4.5, or about 5 cm, or a combination of any of the foregoing values, or a range encompassing any of the foregoing values.

Base Layer

In one aspect, in the simulated tissue disclosed herein, the base layer has a thickness of from about 0.2 cm to about 1.5 cm, or of about 0.2, 0.3, 0.4, 0.5, 0.6, 0.7, 0.8, 0.9, 1, 1.1, 1.2, 1.3, 1.4, or about 1.5 cm, or a combination of any of the foregoing values, or a range encompassing any of the foregoing values.

In some aspects, the base layer further includes a flesh-toned pigment. In other aspects, the skin layer can include other combinations of pigments to represent different colors of flesh (e.g., brown, yellow undertones, green undertones, red undertones) to simulate different races.

Method for Constructing a Simulated Tissue

Disclosed herein are methods for constructing the simulated tissue. In one aspect, the simulated tissue can be constructed as two separate pieces which are later adhered together. In an alternative aspect, the simulated tissue can be constructed in three or more pieces, or layer-by-layer in one piece, or the like.

In one aspect, a vessel such as, for example, an artery or vein, can be constructed by pouring a silicone material over a straw in one or more layers. Further in this aspect, the straw can be removed. If desired, in some aspects, the cured silicone vein can be filled with a colored liquid to simulate blood. In some aspects, the colored liquid is water and is dyed with standard food dyes (e.g., red or blue). In some aspects, the simulated vessels can be sealed at the ends with a compatible adhesive and allowed to dry. In other aspects, the simulated vessels are placed in the simulated tissue in any layer where such vessels would typically be found and fixed into place at the ends with a compatible adhesive.

In another aspect, tumors can be constructed by filling a small balloon with water or other gelatinous substances until the balloon is approximately the desired tumor size and texture.

In one aspect, a silicone material as described herein is poured into the bottom of a mold and allowed to dry, followed by placement of the simulated vessels and any simulated tumors desired. Following this, in some aspects, a mesh material can be laid over the simulated vessels and/or simulated tumor and fixed into place with a thin layer of silicone that can be modified with a pigment if desired. This layered system is referred to as the "base layer."

In another aspect, a mixture of silicone and tactile modifier, which can optionally be colored with pigment, can be poured into a second mold having the same size and shape as the first mold and allowed to cure to form a skin layer. Following this, in another aspect, a silicone material and tactile modifier, with the same or different proportions as for the skin layer, can be poured on top of the skin layer. In some aspects, the fat layer is colored with a yellow pigment. In other aspects, the fat layer is stirred after partially curing to create lumps to simulate fatty tissue.

In still another aspect, following curing of the fat layer, additional silicone material can be poured on top of the fat layer. In some aspects, this material can be colored with a red pigment and is meant to simulate muscle. In one aspect, another mesh material can be laid over the mold so that the mesh material sticks to the underlying layers, which are then allowed to fully dry. This layered system is referred to as the "skin layer."

In one aspect, following assembly of the simulated tissue in two separate parts, the skin layer and/or base layer can be coated by silicone having a tackifier modifier component, with or without pigment, and the skin layer can be placed on top of the base layer, in contact with the uncured silicone. In some aspects, pressure is applied to eliminate air pockets. In any of these aspects, the uncured silicone is allowed to cure and/or dry following assembly of the completed simulated tissue. The layer formed by silicone and tackifier modifier component for adhering the first and second mesh of the skin and base layers represents the interstitial layer.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

Aspect 1: A simulated tissue comprising
  a. a skin layer comprising a first surface and second surface, wherein the skin layer comprises a silicone rubber and a tactile modifier;
  b. a fat layer comprising a first surface and second surface, wherein the first surface of the fat layer is adjacent to the second surface of the skin layer, and wherein the fat layer comprises a silicone rubber and a tactile modifier;
  c. a muscle layer comprising a first surface and second surface, wherein the first surface of the muscle layer is adjacent to the second surface of the fat layer, and wherein the muscle layer comprises a silicone rubber;
  d. a first mesh comprising a first surface and second surface, wherein the first surface of the first mesh is adjacent to the second surface of the muscle layer;
  e. an interstitial layer comprising a first surface and second surface, wherein the first surface of the interstitial layer is adjacent to the second surface of the first mesh, and wherein the interstitial layer comprises a silicone rubber and a tactile modifier;
  f. a second mesh comprising a first surface and second surface, wherein the first surface of the second mesh is adjacent to the second surface of the interstitial layer;
  g. a structural layer comprising one or more anatomical components adjacent to the second surface of the second mesh; and
  h. a base layer comprising a first surface and second surface, wherein the first surface of the base layer is adjacent to the structural layer, and wherein the base layer comprises a silicone rubber.

Aspect 2: The simulated tissue of aspect 1, wherein the skin layer has a thickness of from about 0.1 cm to about 1 cm.

Aspect 3: The simulated tissue of aspect 1 or 2, wherein the skin layer comprises a mixture of silicone rubber and tactile modifier in a ratio of from 1:1 to 4:1 by volume.

Aspect 4: The simulated tissue in any one of aspects 1 to 3, wherein the skin layer further comprises a flesh-toned pigment.

Aspect 5: The simulated tissue in any one of aspects 1 to 4, wherein the fat layer has a thickness of from about 0.25 cm to about 2 cm.

Aspect 6: The simulated tissue in any one of aspects 1 to 5, wherein the fat layer comprises a mixture of silicone rubber and tactile modifier in a ratio of from 2:1 to 1:2 by volume.

Aspect 7: The simulated tissue in any one of aspects 1 to 6, wherein the fat layer further comprises a yellow-toned pigment.

Aspect 8: The simulated tissue in any one of aspects 1 to 7, wherein the muscle layer has a thickness of from about 0.1 cm to about 1.5 cm.

Aspect 9: The simulated tissue in any one of aspects 1 to 8, wherein the muscle layer further comprises a tactile modifier.

Aspect 10: The simulated tissue in any one of aspects 1 to 9, wherein the muscle layer further comprises a red-toned pigment.

Aspect 11: The simulated tissue in any one of aspects 1 to 10, wherein the first mesh comprises a nylon, polyester, polypropylene, polyvinylidene fluoride, polyurethane, polyethylene, a vinyl coated polyester, a thermoplastic elastomer, or a combination thereof.

Aspect 12: The simulated tissue in any one of aspects 1 to 11, wherein the interstitial layer has a thickness of from about 0.2 cm to about 1 cm.

Aspect 13: The simulated tissue in any one of aspects 1 to 12, wherein the interstitial layer comprises a mixture of silicone rubber and tactile modifier in a ratio of from 2:1 to 1:2 by volume.

Aspect 14: The simulated tissue in any one of aspects 1 to 13, wherein the second mesh comprises a nylon, polyester, polypropylene, polyvinylidene fluoride, polyurethane, polyethylene, a vinyl coated polyester, a thermoplastic elastomer, or a combination thereof.

Aspect 15: The simulated tissue in any one of aspects 1 to 14, wherein the anatomical components are adhered to the second surface of the second mesh with a mixture comprising a silicone rubber and tactile modifier.

Aspect 16: The simulated tissue of aspect 15, wherein the silicone rubber and tactile modifier are present in a ratio of from 2:1 to 1:2 by volume.

Aspect 17: The simulated tissue of aspect 15, wherein the mixture comprising a silicone rubber and tactile modifier further comprises a white-toned pigment.

Aspect 18: The simulated tissue in any one of aspects 1 to 17, wherein the anatomical component comprises a vein, an organ, a tumor, a bone, a duct, or any combination thereof.

Aspect 19: The simulated tissue in any one of aspects 1 to 18, wherein the structural layer has a thickness of from about 0.5 cm to about 5 cm.

Aspect 20: The simulated tissue in any one of aspects 1 to 19, wherein the base layer has a thickness of from about 0.2 cm to about 1.5 cm.

Aspect 21: The simulated tissue in any one of aspects 1 to 20, wherein the base layer further comprises a flesh-toned pigment.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example: Construction of the Simulated Tissue

Materials

ECOFLEX™ 00-20 (Smooth-On, Macungie, PA), SLACKER TACTILE MUTATOR® (Reynolds Advanced Materials, Macungie, PA), SILC PIG™ pigments (Smooth-On, Macungie, PA) in flesh, blood, red, yellow, and white colors, and SIL-POXY™ (Smooth-On, Macungie, PA) were purchased from the respective manufacturers and used as received. Plastic straws, blue food coloring, red food coloring, square molds, a colored water balloon, and pantyhose were also used in the construction of the simulated tissue.

Construction of Simulated Vessels and Tumor

Colorless ECOFLEX™ 00-20 was poured over a straw meant to form an even coat, which was allowed to drip dry. A second layer was poured over the simulated vessel to thicken the vessel wall. When dry, the simulated vessel was removed from the straw and filled with colored water. Red food coloring was used in the water to simulate arteries and blue food coloring was used in the water to simulate veins. The ends of the vessels were sealed with SIL-POXY™ and allowed to dry. Separately, a colored water balloon was filled with water to the desired size of the tumor. A typical layer was 1-5 cm thick.

Creation of the Base Layer

ECOFLEX™ 00-20 mixed with flesh-toned SILC PIG™ was poured in the bottom of the square mold and allowed to dry fully. The water balloon representing a tumor was placed in the center of the base. The simulated veins and arteries were stretched over the tumor and glued into place at the ends with SIL-POXY™. A section of nylon pantyhose was cut to the size of the mold and laid over the simulated vessels and tumor. A small amount of ECOFLEX™ 00-20 was mixed in equal parts with SLACKER TACTILE MUTATOR® and tinted with white SILC PIG™ pigment. This mixture was poured in a thin layer over the mesh to cause the mesh to adhere to the structures below and was allowed to dry. A typical layer was approximately 0.5-1 cm thick.

Creation of Skin Layers

A 2:1 mixture of ECOFLEX™ 00-20 and SLACKER TACTILE MUTATOR® colored with flesh-toned SILC PIG™ was poured into a second square mold having the same size as the first square mold and allowed to fully dry. A typical layer was 0.25 to 0.75 cm in thickness.

A 1:1.5 mixture of ECOFLEX™ 00-20 and SLACKER TACTILE MUTATOR® colored with yellow-toned SILC PIG™ was poured on top of the skin layer to create the fat layer. This was stirred when slightly tacky to create lumps in the fat layer and allowed to dry. A typical layer was 0.5 to 1.5 cm in thickness.

ECOFLEX™ 00-20 colored with red-toned SILC PIG™ was poured into a thin layer on top of the fat layer to create the muscle layer. A section of nylon pantyhose was cut to the size of the mold and laid over the mold so that the pantyhose stuck to the fat layer. The silicone was allowed to fully dry. A typical muscle layer was 0.25 to 0.75 cm in thickness, with the mesh forming a layer about 0.25 to 0.5 cm meant to represent fascia Assembly of the Simulated Tissue When the skin layers were fully dry, they were removed from the mold and adhered to the base layers by applying a thin layer of 1:1 ECOFLEX™ 00-20 and SLACKER TACTILE MUTATOR® with no pigment to the base and setting the skin layer on top with the muscle side down. Slight pressure was applied to ensure the absence of air pockets and the assembly was allowed to fully dry.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A simulated tissue comprising a. a skin layer comprising a first surface and second surface, wherein the skin layer comprises a silicone rubber and a tactile modifier;

b. a fat layer comprising a first surface and second surface, wherein the first surface of the fat layer is adjacent to the second surface of the skin layer, and wherein the fat layer comprises a silicone rubber and a tactile modifier;

c. a muscle layer comprising a first surface and second surface, wherein the first surface of the muscle layer is adjacent to the second surface of the fat layer, and wherein the muscle layer comprises a silicone rubber;

d. a first mesh comprising a first surface and second surface, wherein the first surface of the first mesh is adjacent to the second surface of the muscle layer, wherein the first mesh is composed of a material selected from the group consisting of a nylon, polyester, polypropylene, polyvinylidene fluoride, polyurethane, polyethylene, a vinyl coated polyester, and a thermoplastic elastomer;

e. an interstitial layer comprising a first surface and second surface, wherein the first surface of the interstitial layer is adjacent to the second surface of the first mesh, and wherein the interstitial layer comprises a silicone rubber and a tactile modifier;

f. a second mesh comprising a first surface and second surface, wherein the first surface of the second mesh is adjacent to the second surface of the interstitial layer, wherein the second mesh is composed of a material selected from the group consisting of a nylon, polyester, polypropylene, polyvinylidene fluoride, polyurethane, polyethylene, a vinyl coated polyester, and a thermoplastic elastomer;

g. a structural layer comprising one or more anatomical components adjacent to the second surface of the second mesh; and h. a base layer comprising a first surface and second surface, wherein the first surface of the base layer is adjacent to the structural layer, and wherein the base layer comprises a silicone rubber.

2. The simulated tissue of claim 1, wherein the skin layer has a thickness of from 0.1 cm to 1 cm.

3. The simulated tissue of claim 1, wherein the skin layer comprises a mixture of silicone rubber and tactile modifier in a ratio of from 1:1 to 4:1 by volume.

4. The simulated tissue of claim 1, wherein the skin layer further comprises a flesh-toned pigment.

5. The simulated tissue of claim 1, wherein the fat layer has a thickness of from 0.25 cm to 2 cm.

6. The simulated tissue of claim 1, wherein the fat layer comprises a mixture of silicone rubber and tactile modifier in a ratio of from 2:1 to 1:2 by volume.

7. The simulated tissue of claim 1, wherein the fat layer further comprises a yellow-toned pigment.

8. The simulated tissue of claim 1, wherein the muscle layer has a thickness of from 0.1 cm to 1.5 cm.

9. The simulated tissue of claim 1, wherein the muscle layer further comprises a tactile modifier.

10. The simulated tissue of claim 1, wherein the muscle layer further comprises a red-toned pigment.

11. The simulated tissue of claim 1, wherein the interstitial layer has a thickness of from 0.2 cm to 1 cm.

12. The simulated tissue of claim 1, wherein the interstitial layer comprises a mixture of silicone rubber and tactile modifier in a ratio of from 2:1 to 1:2 by volume.

13. The simulated tissue of claim 1, wherein the anatomical components are adhered to the second surface of the second mesh with a mixture comprising a silicone rubber and tactile modifier.

14. The simulated tissue of claim 13, wherein the silicone rubber and tactile modifier are present in a ratio of from 2:1 to 1:2 by volume.

15. The simulated tissue of claim 13, wherein the mixture comprising a silicone rubber and tactile modifier further comprises a white-toned pigment.

16. The simulated tissue of claim 1, wherein the anatomical component comprises a vein, an organ, a tumor, a bone, a duct, or any combination thereof.

17. The simulated tissue of claim 1, wherein the structural layer has a thickness of from 0.5 cm to 5 cm and the base layer has a thickness of from 0.2 cm to 1.5 cm.

18. The simulated tissue of claim 1, wherein the base layer further comprises a flesh-toned pigment.

* * * * *